United States Patent
Shimamoto

(10) Patent No.: US 9,766,451 B2
(45) Date of Patent: Sep. 19, 2017

(54) METHOD FOR CALCULATING SCANNING PATTERN OF LIGHT, AND OPTICAL SCANNING APPARATUS

(71) Applicant: OLYMPUS CORPORATION, Tokyo (JP)

(72) Inventor: Atsuyoshi Shimamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/238,848

(22) Filed: Aug. 17, 2016

(65) Prior Publication Data
US 2017/0045734 A1 Feb. 16, 2017

Related U.S. Application Data

(63) Continuation of application No. PCT/JP2015/055727, filed on Feb. 20, 2015.

(30) Foreign Application Priority Data

Feb. 21, 2014 (JP) ................. 2014-031815

(51) Int. Cl.
*G02B 6/26* (2006.01)
*G02B 26/10* (2006.01)
(Continued)

(52) U.S. Cl.
CPC ........ *G02B 26/103* (2013.01); *A61B 1/00006* (2013.01); *A61B 1/00172* (2013.01);
(Continued)

(58) Field of Classification Search
CPC .. G02B 26/103; G02B 23/2469; G02B 23/26; H02N 2/008; A61B 1/00172; A61B 1/07; A61B 1/00006
See application file for complete search history.

(56) References Cited

U.S. PATENT DOCUMENTS

| 9,639,934 B2* | 5/2017 | Johnston | .................. G06T 7/11 |
| 2008/0058629 A1* | 3/2008 | Seibel | .................. A61B 1/0008 |
| | | | 600/368 |

FOREIGN PATENT DOCUMENTS

| JP | H10-282452 A | 10/1998 |
| JP | 2008-514342 A | 5/2008 |
| JP | 2011-217836 A | 11/2011 |

OTHER PUBLICATIONS

International Search Report dated May 26, 2015 issued in PCT/JP2015/055727.

* cited by examiner

*Primary Examiner* — Ellen Kim
(74) *Attorney, Agent, or Firm* — Scully, Scott, Murphy & Presser, P.C.

(57) ABSTRACT

Provided is a method for calculating a scanning pattern of light and an optical scanning apparatus. The method includes the steps of: detecting a resonance frequency and an attenuation coefficient of an oscillation part of an optical fiber which guides light from a light source and irradiates an object with the light; and calculating a scanning pattern of the light, based on the detected resonance frequency and attenuation coefficient. The apparatus includes: an optical fiber which guides light from a light source and irradiates an object with the light; a scanning part which drives an oscillation part oscillatably supported of the optical fiber; a detector which detects a resonance frequency of the oscillation part; a calculation part which determines an irradiation position of the light using a scanning pattern calculated based on the resonance frequency detected by the detector and the attenuation coefficient obtained in advance.

20 Claims, 18 Drawing Sheets

(51) Int. Cl.
  *G02B 23/24* (2006.01)
  *G02B 23/26* (2006.01)
  *A61B 1/00* (2006.01)
  *A61B 1/07* (2006.01)
  *H02N 2/00* (2006.01)
(52) U.S. Cl.
  CPC ............ *A61B 1/07* (2013.01); *G02B 23/2469* (2013.01); *G02B 23/26* (2013.01); *H02N 2/008* (2013.01)

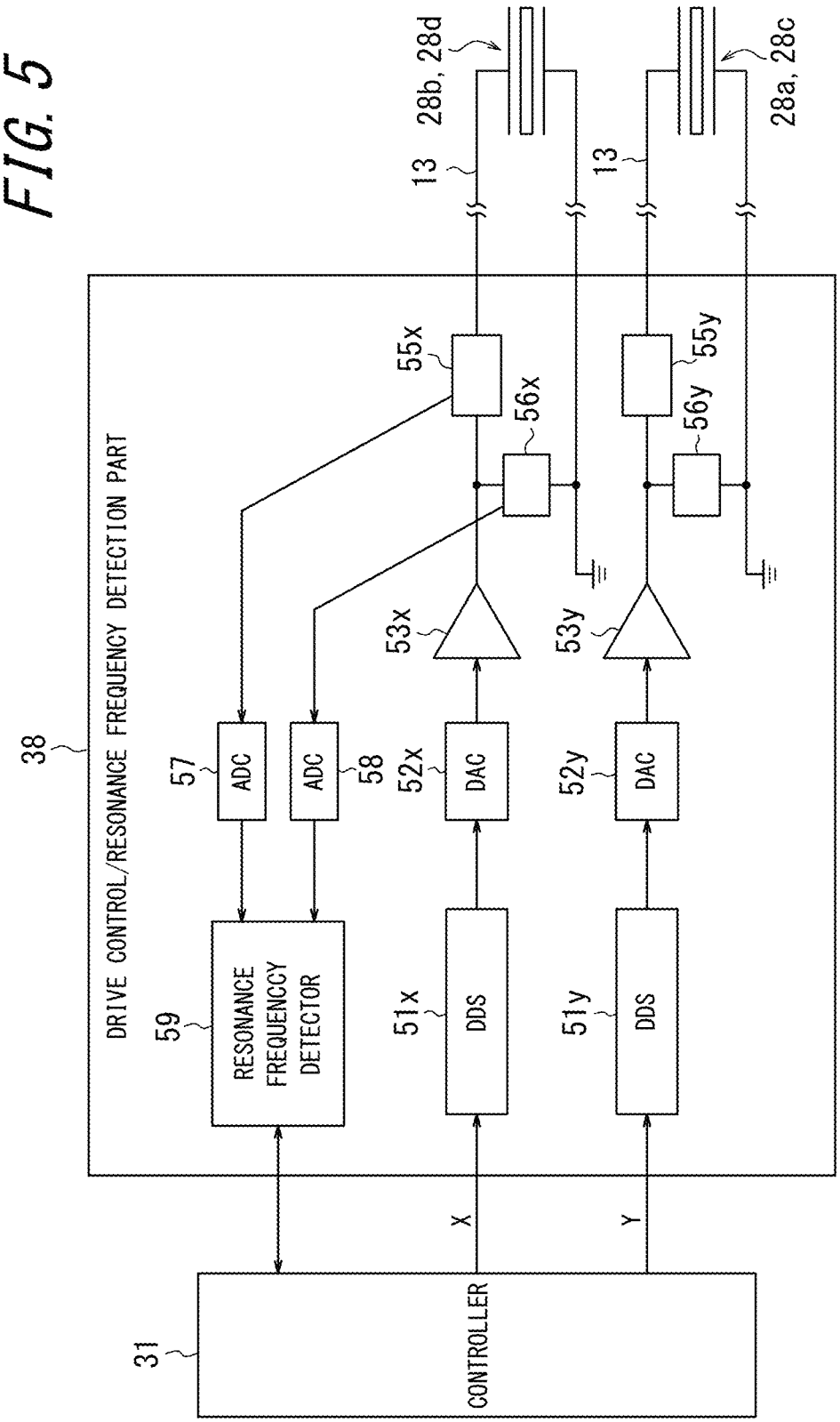

PARTIALLY ENLGRGED

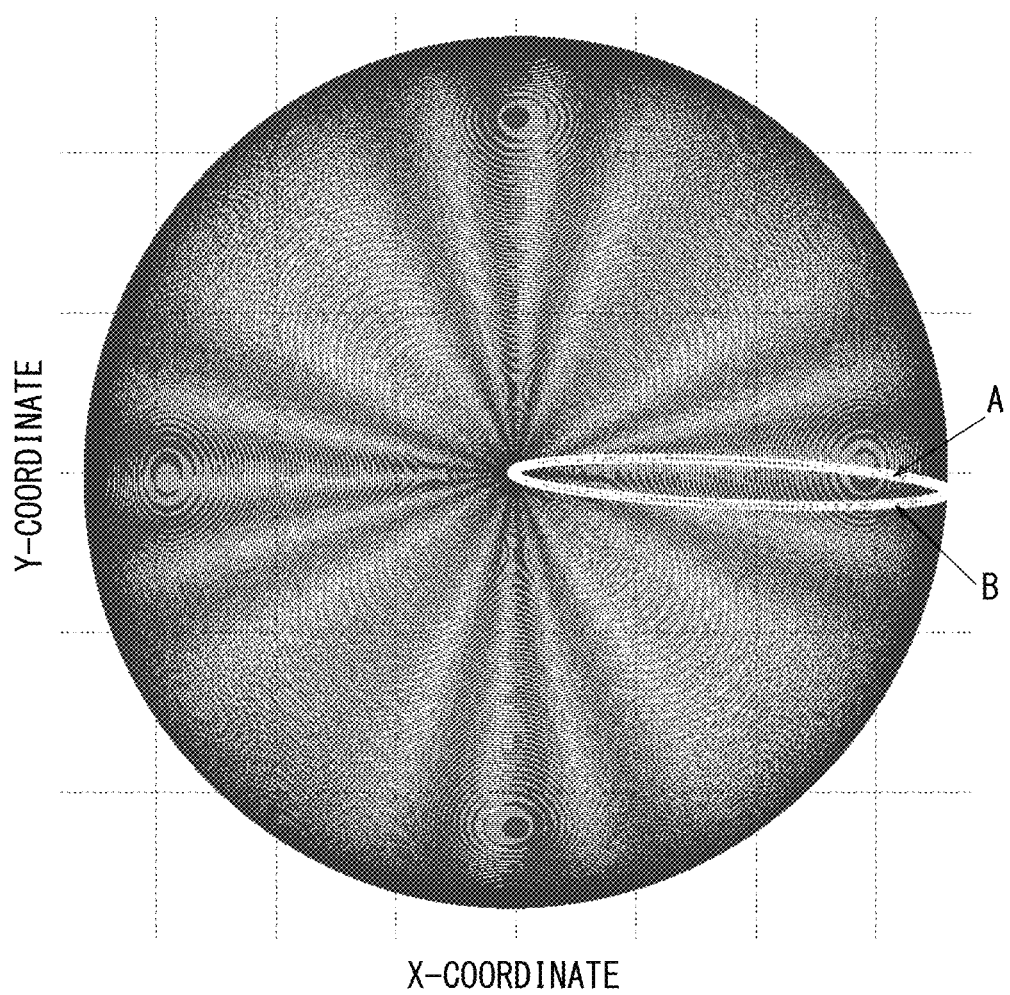

FIG. 16A
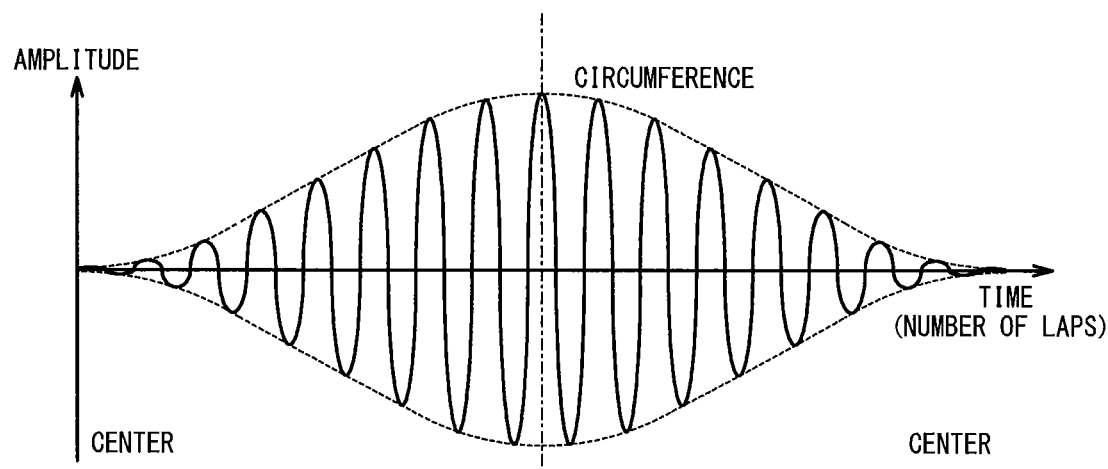
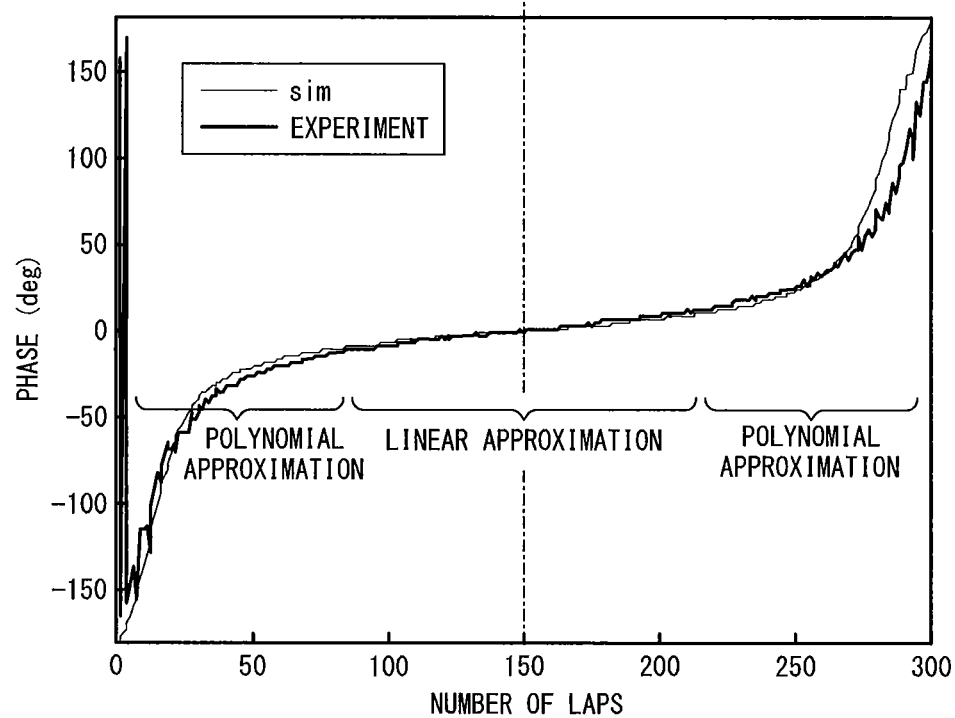
FIG. 16B

METHOD FOR CALCULATING SCANNING PATTERN OF LIGHT, AND OPTICAL SCANNING APPARATUS

CROSS REFERENCE TO THE RELATED APPLICATION

The present disclosure claims priority from Japanese Patent Application No. 2014-031815 filed on Feb. 21, 2014, the entire disclosure of which is incorporated herein by reference.

TECHNICAL FIELD

The present disclosure relates to a method for calculating a scanning pattern of light in scanning endoscopes and an optical scanning apparatus such as a scanning endoscope.

BACKGROUND ART

There has been hitherto known an fiber scanning observation apparatus which scans light from an emitting end of an optical fiber toward an object and detects light reflected or scattered by the object or fluorescence or the like generated in the object. In such apparatus, in order to scan the irradiated light on the object, the optical fiber is cantilevered at the tip part thereof, with the emitting end for emitting light being in an oscillatable state, and a drive mechanism such as a piezoelectric element is disposed so as to exert a force in the vicinity of the supporting part, to thereby vibrate the optical fiber.

Helical scan (spiral scan) and Raster scan have been known as exemplary methods of scanning an optical fiber. The spiral scan scans an optical fiber such that the spot of the irradiated light draws spirals. The raster scan vibrates an optical fiber at high speed in one direction while driving the fiber at low speed in other direction perpendicular thereto. In the spiral scan, the vibration frequency is generally set equal to or near the resonance frequency. In the raster scan, the optical fiber may preferably be vibrated near the resonance frequency in the direction of high-speed vibration. For these reasons, the fiber has been conventionally vibratory driven based on the resonance frequency determined based on the design value of the optical fiber scanning apparatus.

Further, in an optical fiber scanning apparatus, sensors for detecting the position of the fiber may be used to obtain beforehand the coordinate data on the irradiation position of light from the optical fiber, as a function of time elapsed from the start of the scan, and in the actual scan of the object, pixel signals detected according to the time elapsed from the start of the scan are mapped on a two-dimensional coordinate, to thereby generate an image.

Cited Document 1 describes an invention which uses scanning position detectors such as a position sensor device (PSD) to obtain a coordinate value of the actual scanning pattern and creates a look-up table having information on the coordinate value, based on which a coordinate to be assigned to each pixel is corrected.

CITATION LIST

Patent Literature

PTL 1: JP2008-514342A

SUMMARY

The disclosed method for calculating a scanning pattern of light and the disclosed optical scanning apparatus are generally configured as follows.

The disclosed method for calculating a scanning pattern of light includes the steps of: detecting a resonance frequency and an attenuation coefficient of an oscillation part of an optical fiber which guides light from a light source and irradiates an object with the light; and calculating a scanning pattern of the light, based on the detected resonance frequency and attenuation coefficient.

Further, in the disclosed method for calculating a scanning pattern of light, the scanning pattern may preferably include information on temporal change in phase shift of the oscillation part. Here, the phase refers to an angle of the scanning pattern represented by polar coordinates.

Further, the disclosed method for calculating a scanning pattern of light may preferably further include the step of calculating an approximation function of the temporal change in phase shift.

The disclosed method for calculating a scanning pattern of light according to another aspect includes the steps of: detecting, using position data detected by a scanning position detector, a scanning pattern of light from an oscillation part of an optical fiber which guides the light from a light source and irradiates an object with the light; and calculating an approximation coefficient of temporal change in phase shift of the oscillation part included in the scanning pattern.

Here, in the disclosed method for calculating a scanning pattern of light, the approximation function may preferably be an exponential function when the amplitude of the oscillation part is equal to or lower than a certain value, and may preferably be a first-order function when the amplitude is larger than the certain value.

Further, in the disclosed method for calculating a scanning pattern of light, the approximation function may preferably be a second or higher-order polynomial function when the amplitude of the oscillation part is equal to or smaller than a certain value, and may preferably be a first-order function when the amplitude is larger than the certain value.

Further, in the disclosed method for calculating a scanning pattern of light, the approximation function may preferably be calculated separately for the forward path and the return path of the scanning pattern.

Further, in the disclosed method for calculating a scanning pattern of light, the approximation function may preferably depend on the drive frequency and/or the maximum amplitude of the oscillation part.

Here, the disclosed optical scanning apparatus includes: an optical fiber which guides light from a light source and irradiates an object with the light; a drive control part which drives an oscillation part oscillatably supported of the optical fiber; a resonant frequency detector which detects a resonance frequency of the oscillation part; a calculation part which determines an irradiation position of the light using a scanning pattern calculated based on the resonance frequency detected by the detector and the attenuation coefficient obtained in advance.

Further, in the disclosed optical scanning apparatus, the scanning pattern may preferably include information on temporal change in phase shift of the oscillation part.

Further, in the disclosed optical scanning apparatus, the calculation part may preferably calculate an approximation coefficient of the temporal change in phase shift.

The disclosed optical scanning apparatus according to another aspect includes: an optical fiber which guides light from a light source and irradiates an object with the light; a drive control part which drives an oscillation part oscillatably supported of the optical fiber; and a calculation part which calculates, using position data detected by a scanning position detector, an approximation coefficient of temporal change in phase shift of the oscillation part included in the scanning pattern.

Further, in the disclosed optical scanning apparatus, the approximation function may preferably be an exponential function when the amplitude of the oscillation part is equal to or smaller than a certain value, and may preferably be a first-order function when the amplitude is larger than the certain value.

Furthermore, in the optical scanning apparatus, the approximation function may preferably be a second or higher-order polynomial function when the amplitude of the oscillation part is equal to or smaller than a certain value, and may preferably be a first-order function when the amplitude is larger than the certain value.

Further, in the disclosed optical scanning apparatus, the calculation part calculates the approximation function separately for the forward path and the return path of the scanning pattern.

Further, in the optical scanning apparatus, the approximation function may preferably depend on the drive frequency and/or the maximum amplitude of the oscillation part.

Further, in the disclosed method for calculating a scanning pattern of light, the approximation function may be preferably calculated separately in the case when the amplitude of the oscillation part is equal to or smaller than a certain value and in the case when the amplitude is larger than the certain value.

Further, in the optical scanning apparatus, the approximation function may be preferably calculated separately by the calculation part in the case when the amplitude of the oscillation part is equal to or smaller than a certain value and in the case when the amplitude is larger than the certain value.

BRIEF DESCRIPTION OF DRAWINGS

In the accompanying drawings:

FIG. 5 is a block diagram showing a schematic configuration of the drive control/resonance frequency detection part;

FIG. 15 shows an exemplary scanning pattern calculated when a spiral scan has been performed;

FIG. 16A shows a drive pattern and FIG. 16B shows a relation between the number of laps and the phase;

DESCRIPTION OF EMBODIMENTS

The following illustrates in detail embodiments of the disclosed method and apparatus, with reference to the drawings.

Figure 1:
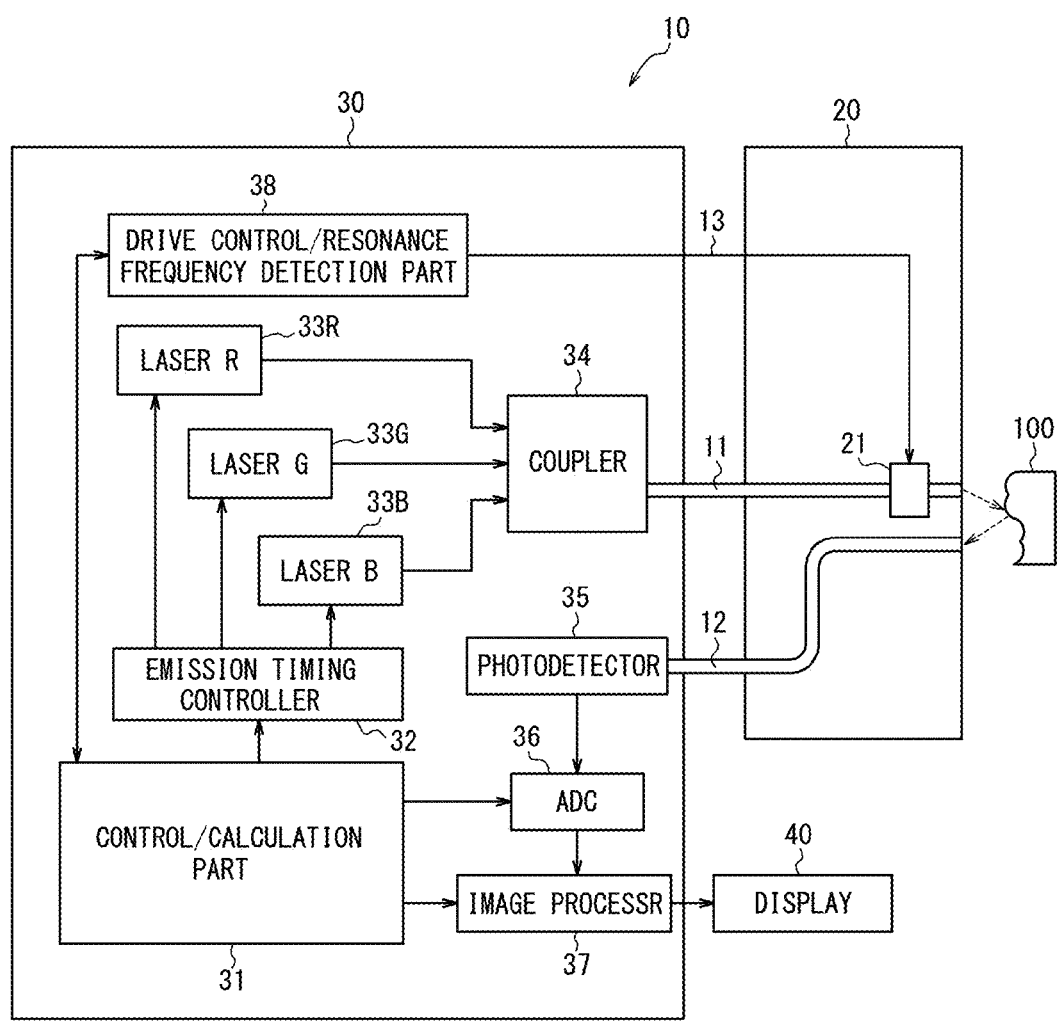
FIG. 1 is a block diagram showing a schematic configuration of an fiber scanning endoscope apparatus as an example of the disclosed optical scanning apparatus according to one embodiment thereof.

First, an example of the disclosed optical scanning apparatus is described with reference to the drawings. FIG. 1 is a block diagram illustrating a schematic configuration of an optical scanning endoscope apparatus as an example of the optical scanning apparatus. The optical scanning endoscope apparatus 10 includes: a scope 20; a control device body 30; and a display 40.

The control device body 30 is configured by including: a control/calculation part 31 controlling across the entire optical scanning endoscope apparatus 10; an emission timing controller 32; lasers 33R, 33G, 33B; and a coupler 34. The emission timing controller 32 controls, under the control of the control/calculation part 31, the emission timings of the three lasers 33R, 33G, 33B emitting laser light of three primary colors of red, green, and blue. Examples for use as the lasers 33R, 33G, 33B may include, for example, a diode pumped solid state (DPSS) laser and a laser diode. Laser lights emitted from the lasers 33R, 33G, 33B are multiplexed by the coupler 34, and caused to incident, as white illumination light, on an illumination optical fiber 11 being a single mode fiber. Needless to say, the light sources of the optical scanning endoscope apparatus 10 may not be limitedly configured as above; the apparatus 10 may use one laser light source or a plurality of other light sources. Further, the lasers 33R, 33G, 33B and the coupler 34 may be accommodated in another casing which is different from the control device body 30 but connected with the control device body 30 via a signal line.

The illumination optical fiber 11 is linked to the tip part of the scope 20, and light incident on the illumination optical fiber 11 from the coupler 34 is guided to the tip part of the scope 20 and irradiated toward an object 100. At this time, an actuator 21 is vibratory driven, so as to two-dimensionally scan an observation surface of the object 100 with illumination light emitted from the illumination optical fiber 11. The actuator 21 is controlled by a drive control/resonance frequency detection part 38 of the control device body 30 to be described later. The object 100 irradiated with the illumination light provides signal light such as reflected light, scattered light, and fluorescence, which are received at the tip of a detection optical fiber bundle 12 formed of multimode fibers and guided through the scope 20 to the control device body 30.

The control device body 30 further includes a photodetector 35, an analog-to-digital converter (ADC) 36, and an image processor 37, which are for processing signal light. The photodetector 35 splits signal light that has passed through the detection optical fiber bundle 12 into spectral components, and converts the spectral components into electric signals by using photodiodes. The image signals having been converted into electric signals are converted into digital signals by the ADC 36, which then outputs the digital signals to the image processor 37. The control/calculation part 31 calculates, based on information on the amplitude and phase of the vibration voltage applied by the drive control/resonance frequency detection part 38, information on the scanning position on the scanning path, and passes the information to the image processor 37. The image processor 37 obtains, from the digital signals output from the ADC 36, pixel data of the object 100 at the scanning position. The image processor 37 sequentially stores, in a memory (not shown), information on the scanning position and the pixel data, performs necessary process such as interpolation process on the data during or after the scan to generate an image of the object 100, and displays the image on the display 40.

In each of the aforementioned processes, the control/calculation part 31 synchronously controls the emission timing controller 32, the photodetector 35, the drive control/resonance frequency detection part 38, and the image processor 37.

Figure 2:
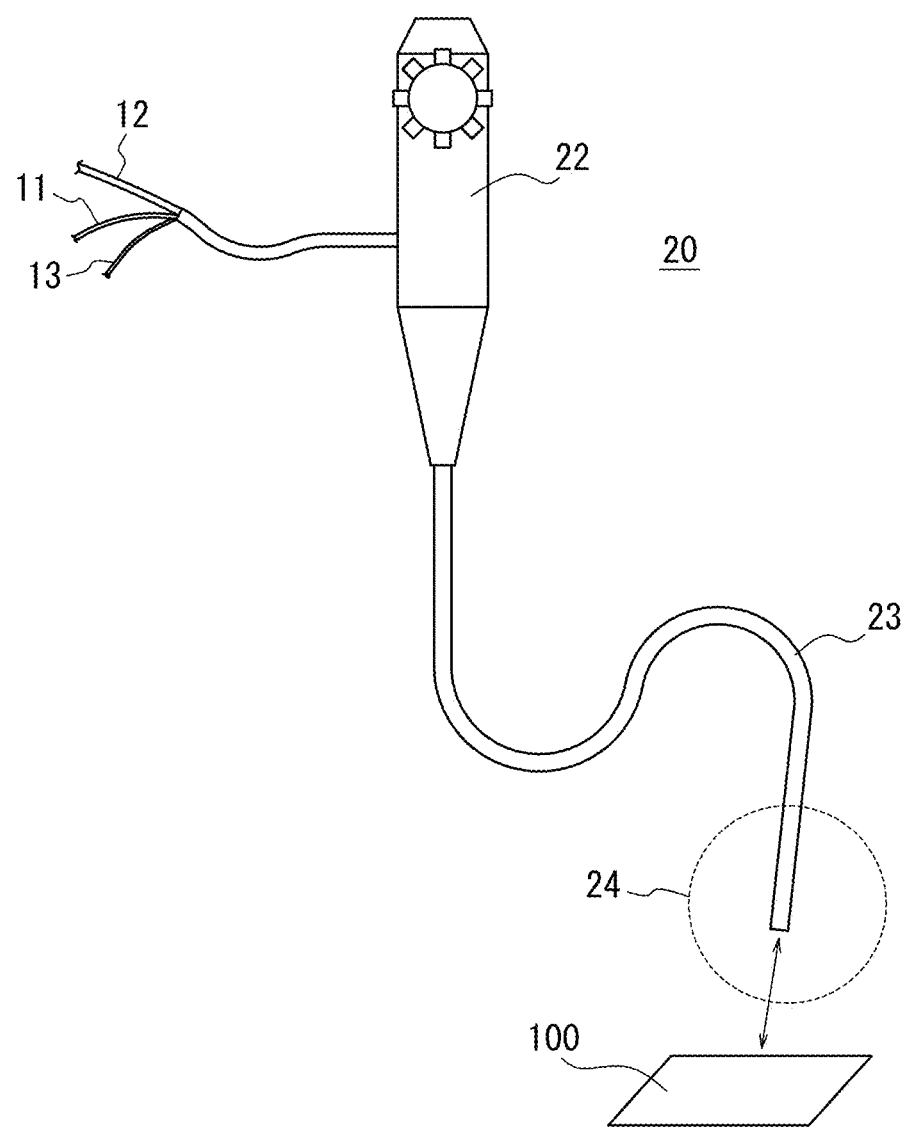
FIG. 2 is an overview schematically illustrating the scope of the fiber scanning endoscope apparatus of FIG. 1.

FIG. 2 is an overview schematically illustrating the scope 20. The scope 20 includes the operating portion 22 and the insertion portion 23. The illumination optical fiber 11, the detection optical fiber bundle 12, and the wiring cable 13 from the control device body 30 are each connected to the operating portion 22. The illumination optical fiber 11, the detection optical fiber bundle 12, and the wiring cable 13 extend through inside the insertion portion 23 to be guided to the tip part 24 (enclosed by the dashed line of FIG. 2) of the insertion portion 23.

Figure 3:
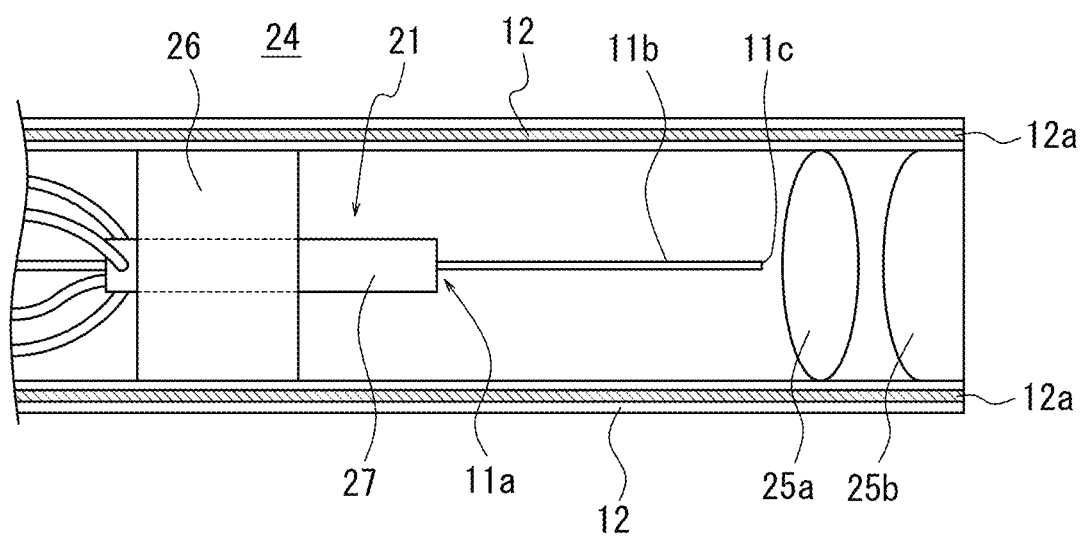
FIG. 3 is a sectional view of the tip part of the scope of FIG. 2.

FIG. 3 is an enlarged sectional view of the tip part 24 of the insertion portion 23 of the scope 20 of FIG. 2. The tip part 24 is configured by including: the actuator 21; projection lenses 25a, 25b; the illumination optical fiber 11 passing through the central part; and the detection optical fiber bundle 12 passing through the circumferential part.

The actuator 21 is configured by including: an actuator tube 27 fixed inside the insertion portion 23 of the scope 20 through an attachment ring 26; and a fiber holding member 29 and piezoelectric elements 28a to 28d (see FIGS. 4A and 4B) disposed within the actuator tube 27. The illumination optical fiber 11 is held by the fiber holding member 29, and has an oscillation part 11b oscillatably supported, the oscillation part 11b being defined between an fixed end 11a held by the fiber holding member 29 and the tip part 11c. Meanwhile, the detection optical fiber bundle 12 is disposed so as to pass through the circumferential part of the insertion portion 23 to extend to the tip of the tip part 24. Further, the detection optical fiber bundle 12 may include a detection lens, which is not shown, at the tip part of each fiber.

Further, the projection lenses 25a, 25b and the detection lens are disposed at the extreme tip of the tip part 24. The projection lenses 25a, 25b are configured such that laser light emitted from the tip part 11c of the illumination optical fiber 11 is substantially converged onto the object 100.

Further, the detection lens is disposed to take in the laser light that has been reflected, scattered, and refracted by the object 100 (light that has been interacted with the object 100) after being converged onto the object 100, so as to converge and couple the laser light to the detection optical fiber bundle 12 disposed behind the detection lens. Here, one projection lens or a plurality of other lenses may constitute the projection lens system, without being limited to the two-lens configuration. The detection fiber bundle may directly take in light without using the detection lens.

Figure 4A:
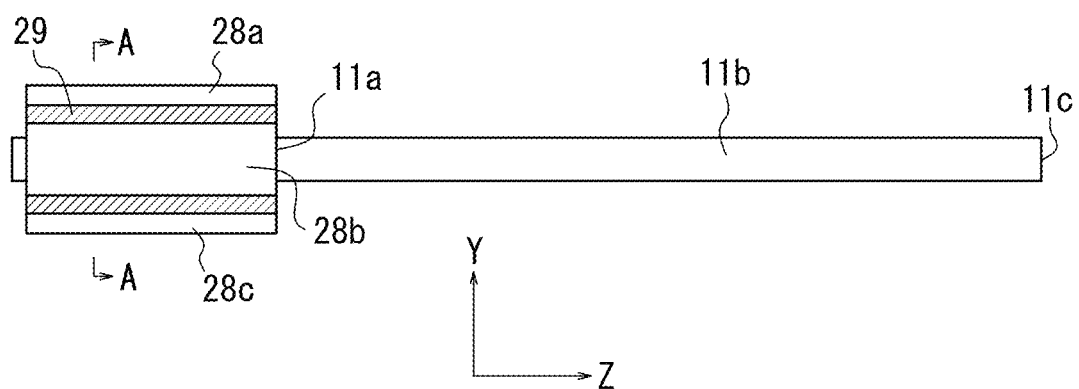
FIGS. 4A and 4B each show a configuration of the actuator of FIG. 3.
Figure 4B:
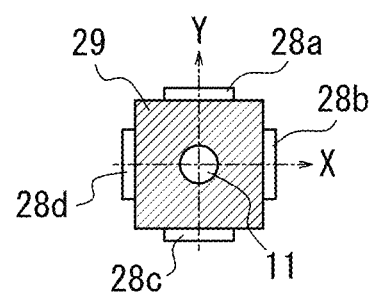

FIG. 4A illustrates a vibratory drive mechanism of the actuator 21 of the optical scanning endoscope device 10 and the oscillation part 11b of the illumination optical fiber 11, and FIG. 4B is a sectional view taken along the line A-A of FIG. 4A. The illumination optical fiber 11 penetrates through the center of the fiber holding member 29 in a prism shape, so as to be fixed and held by the fiber holding member 29. The fiber holding member 29 has four side faces each facing the +Y direction and the +X direction and the directions opposite thereto, respectively, of which two side faces of the fiber holding member 29 facing the +Y direction and −Y direction have a pair of the Y-direction driving piezoelectric elements 28a, 28c fixed thereon, and two side faces of the fiber holding member 29 facing the +X direction and −X direction have a pair of the X-direction driving piezoelectric elements 28b, 28d fixed thereon.

The piezoelectric elements 28a to 28d are each connected with the wiring cables 13 from the drive control/resonance frequency detection part 38.

Here, referring again to FIG. 1, the control device body 30 includes the drive control/resonance frequency detection part 38 for detecting the resonance frequency of the oscillation part 11b of the optical fiber 11. The drive control/resonance frequency detection part 38 may detect the resonance frequency by a simple method such as, for example, impedance measurement for monitoring a current value to be obtained when a predetermined voltage is applied to the piezoelectric elements.

FIG. 5 is a block diagram showing a schematic configuration of the drive control/resonance frequency detection part 38.

For driving the piezoelectric elements 28a to 28d of the actuator 21, the drive control/resonance frequency detection part 38 includes: a direct digital synthesizers (DDS) 51x, 51y; a digital-to-analog converters (DAC) 52x, 52y; and amplifiers 53x, 53y. The DDS 51x and the DDS 51y each receive a control signal from the control/calculation part 31 and generate a digital drive signal waveform. The signal is converted into an analog signal by the DAC 52x, 52y, amplified by the amplifiers 53x, 53y, and drives, via the wiring cable 13, the piezoelectric elements 28a to 28d disposed at the tip part 24 of the scope 20.

In practice, however, a voltage of the same magnitude and opposite polarity is always applied across the X-direction piezoelectric elements 28b and 28d. Similarly, a voltage of the same magnitude and opposite polarity is always applied across the Y-direction piezoelectric elements 28a and 28c. Of the piezoelectric elements 28b, 28d disposed opposite to each other across the fiber holding member 29, one is extended while the other is contracted in an alternating manner to deflect the fiber holding member 29, which may be repeated to cause vibration in the X direction. The same applies to the vibration in the Y direction.

The drive control/resonance frequency detection part 38 may vibratory drive the X-direction-drive piezoelectric elements 28b, 28d and the Y-direction-drive piezoelectric elements 28a, 28c by applying thereto vibration voltages of the same frequency or vibration voltages of different frequencies. When the Y-direction-drive piezoelectric elements 28a, 28c and the X-direction-drive piezoelectric elements 28b, 28d are each vibrately driven, the oscillation part 11b of the illumination optical fiber 11 is vibrated to deflect the tip part 11c, which causes laser light emitted from the tip part 11c to sequentially scan the surface of the object 100.

The oscillation part 11b of the illumination optical fiber 11 is vibratory driven both in the X and Y directions at the resonance frequency. However, the resonance frequency of the oscillation part 11b varies due to the environmental conditions and lapse of time, and thus the drive control/resonance frequency detection part 38 has a resonance frequency detection mechanism for detecting the resonance frequency of the oscillation part 11b of the illumination optical fiber 11. The resonance frequency detection mechanism includes, as illustrated in FIG. 5, a current detection circuit 55x and a voltage detection circuit 56x disposed on a circuit extending from the amplifier 53x toward the piezoelectric elements 28b, 28d; analog-to-digital converters (ADC) 57, 58 for converting the current signal and the voltage signal detected by the circuits 55x, 56x into digital signals; and a resonance frequency detector 59 detecting the resonance frequency of a vibration in the X direction based on the phase difference between the output signals from the two ADC 57 and ADC 58. Here, a current detection circuit 55y and a voltage detection circuit 56y are similarly provided in order to detect the resonance frequency of vibration in the Y direction, which are also configured to have the outputs thereof to be input to the resonance frequency detector 59 via ADC (not shown).

Described next is how the drive control/resonance frequency detection part 38 measures impedance.

The X-direction piezoelectric elements 28b, 28d and the Y-direction piezoelectric elements 28a, 28c are applied with vibration voltages having an amplitude equal to a predetermined amplitude, shifted in phase by 90° in the X direction and the Y direction, and having a frequency f that increases with time. This way causes the vibration frequency of the tip part 11c of the illumination optical fiber 11 to sweep within a predetermined frequency range. The predetermined frequency range is determined by predicting in advance a range in which the resonance frequency may vary in the neighborhood of the designed resonance frequency.

Figure 6A:
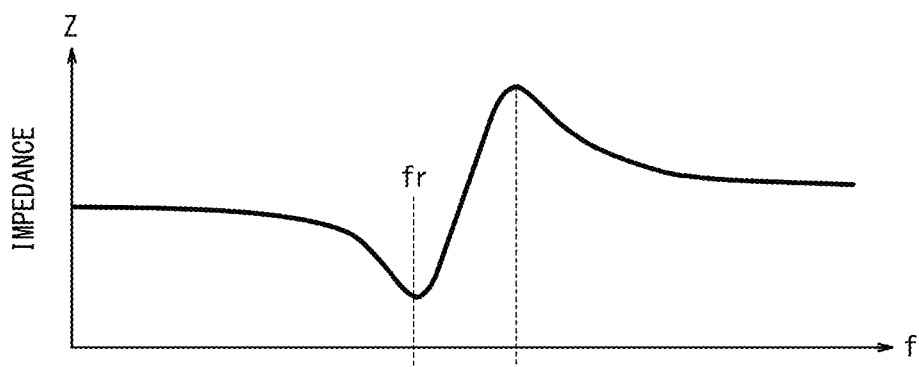
FIGS. 6A and 6B are graphs showing typical frequency characteristics of impedance and phase shift.
Figure 6B:
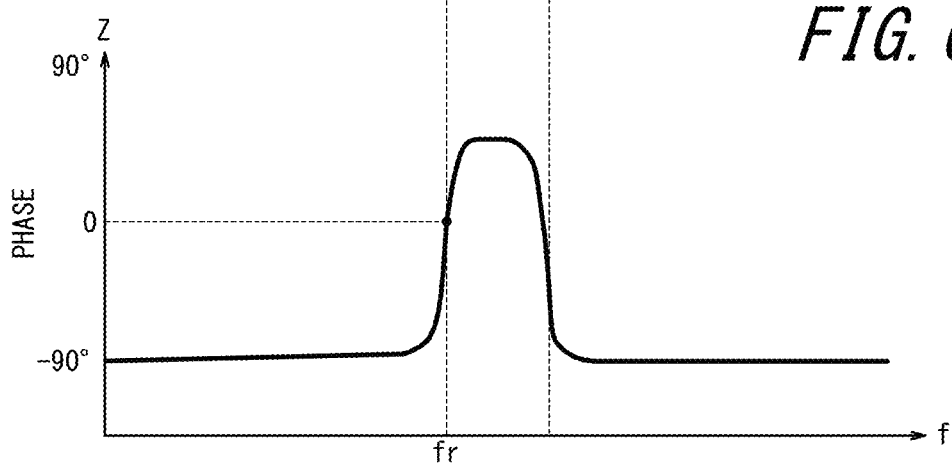

During the increase of the frequency of the drive voltage, the resonance frequency detector 59 monitors the current signal and the voltage signal each detected by the current detection circuits 55x, 55y and the voltage detection circuits 56x, 56y, respectively. The resonance frequency detector 59 senses phase shifts in the current signal and the voltage signal to thereby detect the resonance frequency. In general, the frequency characteristics of the impedance of the vibration circuit and of the phase shift in current and voltage are each known to be obtained as those illustrated in FIGS. 6A and 6B, respectively. As illustrated in FIG. 6A, when vibrated at the resonance frequency, the impedance reaches its minimum and the phase shift turns to zero. Thus, the resonance frequency detector 59 identifies, as the resonance frequency, a frequency fr obtained when the phase shift between the current signal from the current detection circuits 55x, 55y and the voltage signal from the voltage detection circuits 55x, 56y turns to zero, and outputs the resonance frequency thus identified to the control/calculation part 31. Further, the aforementioned measurement method can obtain other various measurement values from a dynamic admittance circle which is the admittance of the piezoelectric elements represented on a complex plane, and a mechanical series resonance frequency fs may be identified as the resonance frequency.

Further, as to the attenuation coefficient (Q value), impedance measurement or the like allows for calculating in advance the attenuation coefficient. In this embodiment, the resonance frequency and the attenuation frequency may be detected by a shared detector or by separate detectors.

Further, this embodiment has exemplified an actuator using piezoelectric elements, the same method may also be used in an actuator of electromagnetic driving type to detect the resonance frequency and the attenuation coefficient.

Figure 7A:
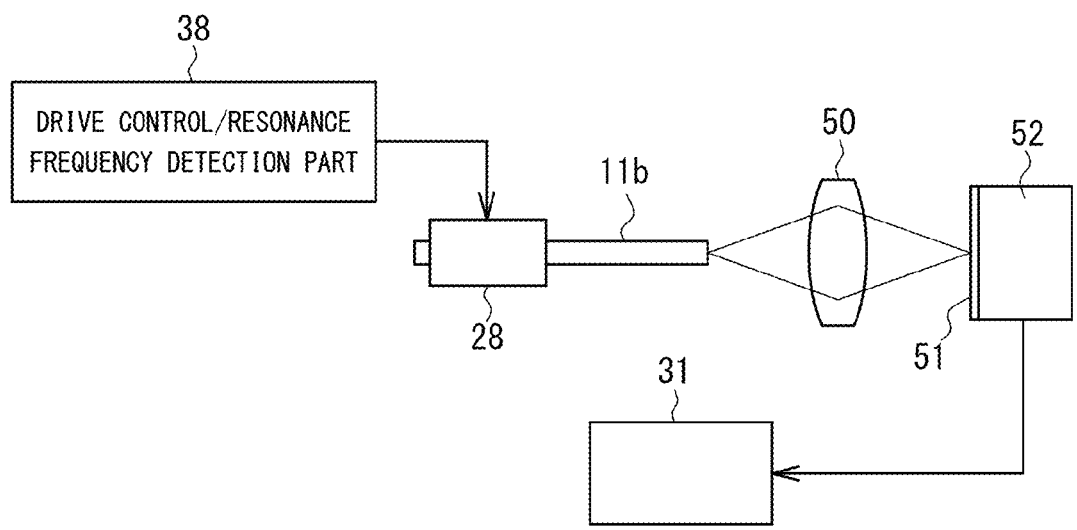
FIG. 7A shows a mechanism for measuring frequency characteristics for a drive signal at the scanning amplitude of the fiber.
Figure 7B:
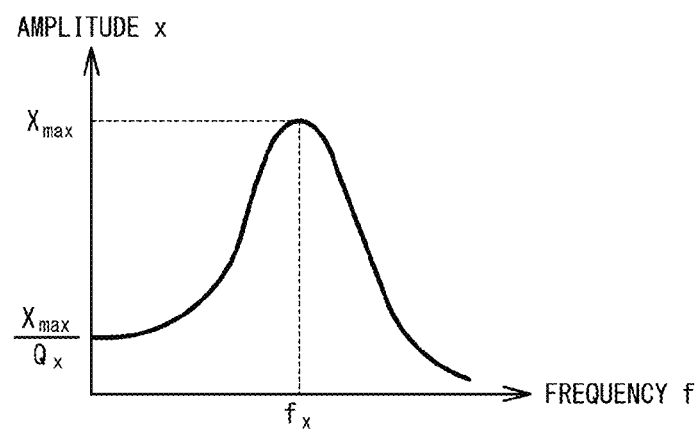
FIG. 7B is a graph showing the frequency characteristics.

Further, as illustrated in FIGS. 7A and 7B, frequency characteristics relative to the drive signal at the scanning amplitude of the optical fiber may be measured to obtain the resonance frequency, the maximum amplitude, and the attenuation coefficient (Q value) of the fiber.

In other words, as illustrated in FIG. 7A, the drive control/resonance frequency detection part 38 may give a periodic drive waveform having a constant amplitude to the piezoelectric element 28, to thereby drive the oscillation part 11b of the fiber. Light is guided through the fiber and emitted from the fiber emitting end, which is then focused, through an optical system 50, onto a light detection surface 51 of the optical scanning position detector 52.

In this manner, the amplitude value of the fiber may be measured by sweeping the frequency of the drive waveform, so as to obtain the graph as shown in FIG. 7B.

Based on the frequency characteristics of the amplitude, the resonance frequency fx in a certain driving direction (X) of the fiber and the maximum amplitude Xmax of the fiber can be obtained.

Further, the amplitude x of a cantilevered fiber vibration is ideally represented by the following equation:

$$x = \frac{X\max}{\sqrt{\left(\frac{f}{fx}\right)^2 + Qx^2\left\{1 - \left(\frac{f}{fx}\right)^2\right\}}} \quad \text{(Equation 1)}$$

Equation 1 above may be used to obtain Q value (Qx) of the vibration. The relation between the attenuation coefficient ζx and Q value (Qx) is represented by Equation 2 below;

$$Qx = \frac{1}{2\zeta x} \quad \text{(Equation 2)}$$

As in the case of the X direction, the resonance frequency fy, the maximum amplitude Ymax, and Q value (Qy) can be obtained for the Y direction.

The method for measuring the amplitude is not limited to the aforementioned example. For example, an image sensor may be used in place of the PSD, or the vibratory displacement of the oscillation part 11b of the fiber may be measured by a laser displacement meter. Alternatively, the drive signal for scanning an optical fiber is set to zero at a certain time, so as to analyze the attenuation curve of the damping oscillation of the fiber, to thereby obtain the resonance frequency and the attenuation coefficient (Q value) of the fiber.

Further, as illustrated in FIG. 1, the control/calculation part 31 may calculate the scanning pattern of light, based on the attenuation coefficient; the resonance frequency detected by the drive control/resonance frequency detection part 38; and a selected drive frequency and/or maximum amplitude.

To calculate the scanning pattern by the control/calculation part 31, specifically, the coefficients of the motion equation of the oscillation part 11*b* may be substituted by the resonance frequency detected by the drive control/resonance frequency detection part 38, the attenuation coefficient obtained in advance, and the scanning amplitude of the fiber, so as to solve the motion equation. The motion equation may be solved analytically and/or numerically. Here, for example, the resonance frequency and the attenuation coefficient may be detected upon shipment of the product to calculate the resonance frequency, or the resonance frequency and the attenuation coefficient may be detected after having changed due to aging.

Figure 8:
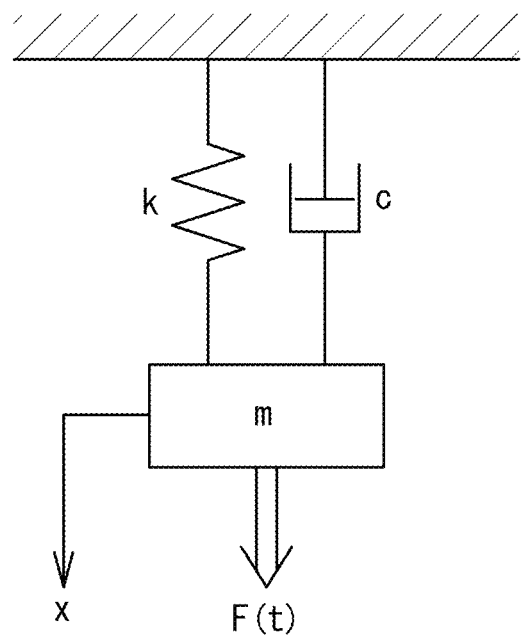
FIG. 8 shows a Mass-Spring model.

As illustrated in FIG. 8, the behavior of the resonance vibration of a cantilevered fiber can simply be accounted based on, for example, a Mass-Spring model. The motion equation (Equation 3) below may used to express the vibration of the oscillation part 11*b* of the fiber, in which x represents the amplitude of the oscillation part 11*b* of the fiber.

$$m\ddot{x} = -kx - c\dot{x} + F(t) \quad \text{(Equation 3)}$$

(where m: mass, k: spring coefficient, c: damper coefficient, F(t): external force)

Here, Equation 3 above may be represented as Equation 4 below, in which $\omega = (k/m)^{1/2}$, $Q = 1/(2\zeta) = (mk)^{1/2}/c$, $F(t)/m = K \cdot u(t)$:

$$\ddot{x} + \frac{\omega}{Q} \cdot \dot{x} + \omega^2 \cdot x = K \cdot u(t) \quad \text{(Equation 4)}$$

(where: $\omega = 2\pi f$: natural angular frequency of the fiber, Q=vibration Q value of the fiber, $\zeta$: attenuation coefficient of the fiber, K: gain, u(t): input waveform).

The differential equation (Equation 4) may be Laplace transformed, so as to obtain a transfer function G(s) of the fiber vibration system, which can be expressed by a secondary delay system as shown in Equation 5 below.

$$G(s) = \frac{K}{s^2 + \frac{\omega}{Q} \cdot s + \omega^2} \quad \text{(Equation 5)}$$

In this manner, the resonance frequency, the attenuation coefficient, and the maximum amplitude of the fiber may be obtained, so as to numerically calculate the scanning pattern with respect to an arbitrary drive input waveform.

The scanning pattern thus calculated includes information on temporal change in phase shift, which allows the control/calculation part 31 to calculate an approximation function for the temporal change in phase shift.

As will be described later, as the approximation function, only one function may be obtained across the entire domain of definition (time axis) or different functions may be obtained for each domain of definition.

Here, a method for calculating the approximation function is specifically described.

Figure 9A:
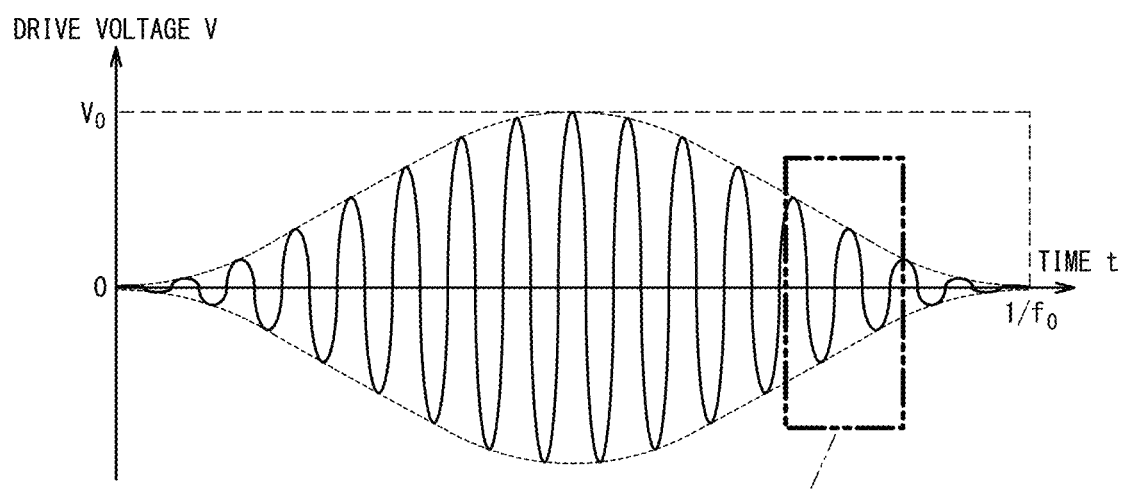
FIG. 9A shows an exemplary drive waveform.

Exemplifying the drive waveform of FIG. 9A, the function of the drive voltage modulation waveform is represented by the following equation:

$$V = \frac{V_0}{2}(1 - \cos(2\pi f_0 t)) \quad \text{(Equation 6)}$$

In the equation, $f_0$ represents the modulation frequency (frame rate/2).

Figure 9B:
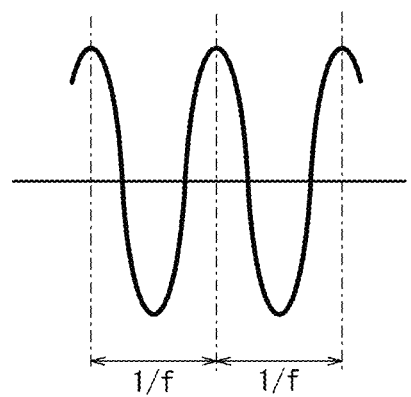
FIG. 9B is a partial enlarged view of FIG. 9A.

FIG. 9B is a partial enlarged view of FIG. 9A, in which f represents the drive frequency.

With the drive waveform above, one image can be obtained at a time in the forward path and the return path of a spiral scan, respectively.

Figure 10A:
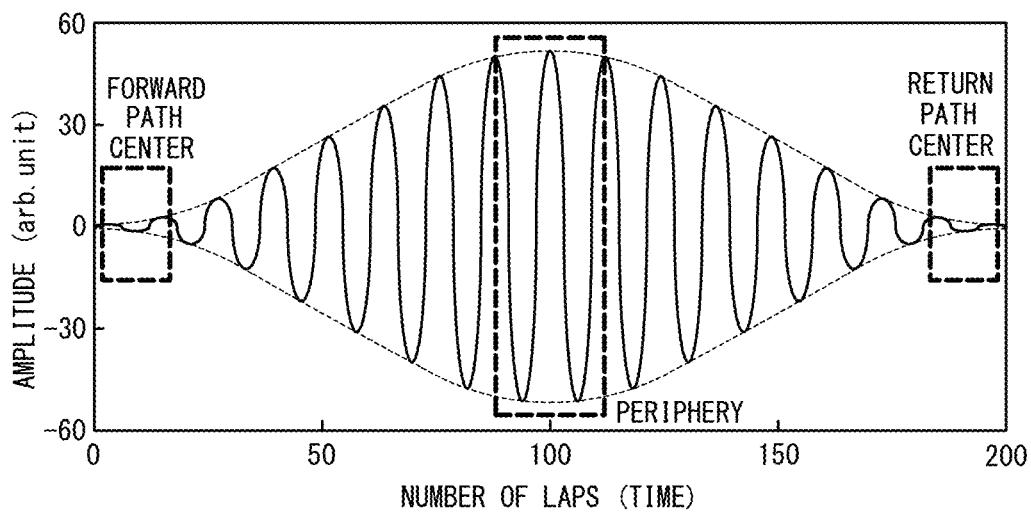
FIG. 10A shows a forward path and a return path of the drive waveform.
Figure 10B:
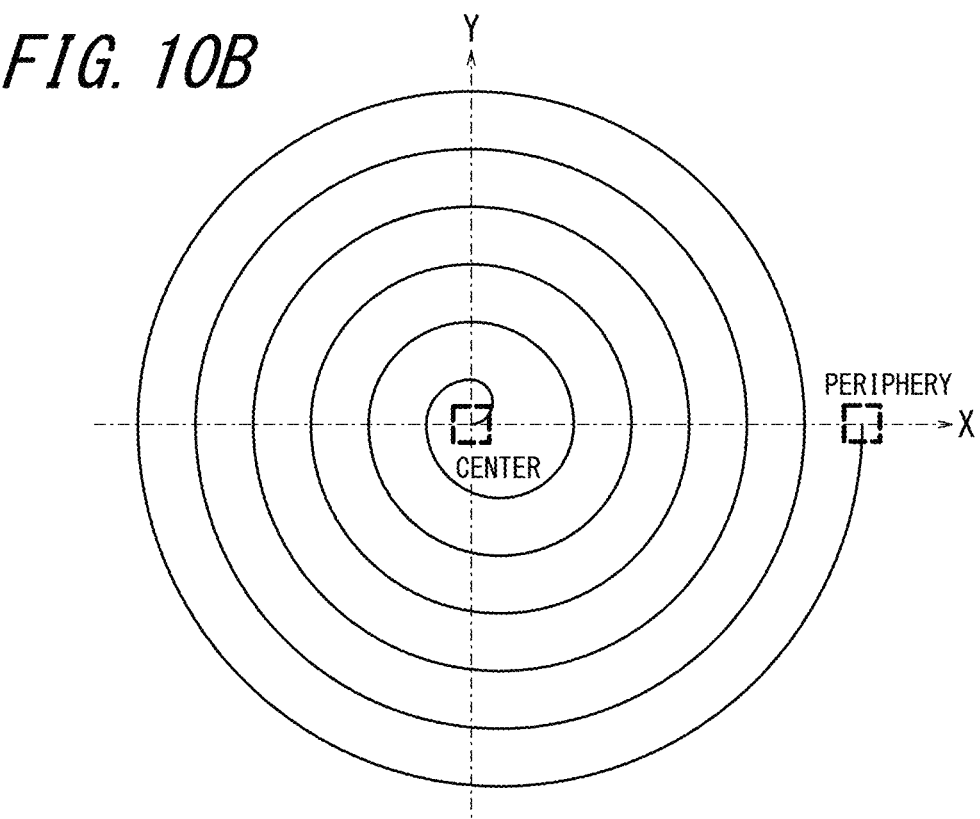
FIG. 10B shows a forward path of the scanning pattern.
Figure 11A:
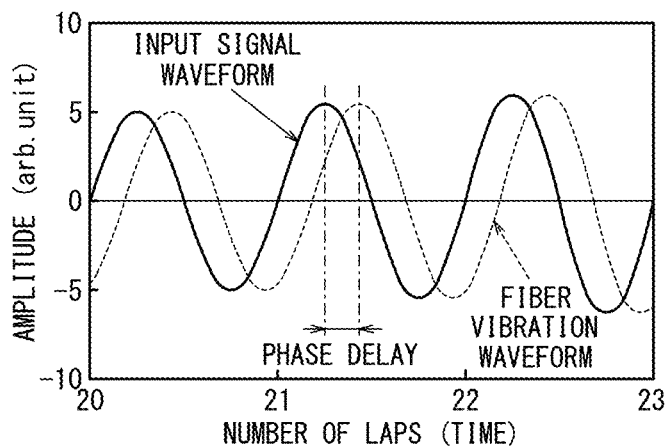
FIGS. 11A to 11C each illustrate variations in phase shift relative to the number of laps.
Figure 11B:
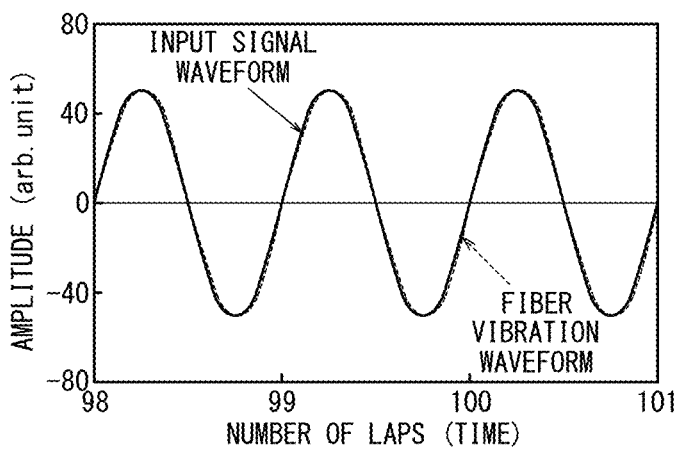
Figure 11C:
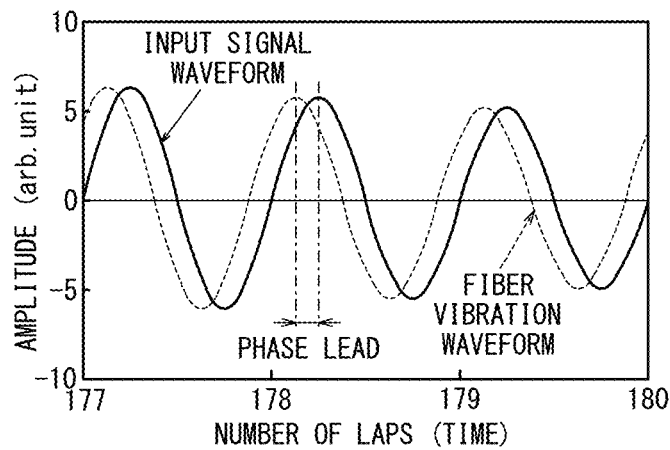

As to the vibration pattern to be obtained in each of the X direction and the Y direction, when comparing the phase shift relative to the input signal waveform, the vibration pattern may be considered separately in the center and the periphery of the forward path as illustrated in FIGS. 10A and 10B. In this case, as illustrated in FIGS. 11A to 11C, the phase shift becomes greater near the center of the scanning pattern while the phase shift becomes smaller near the periphery of the scanning pattern.

Figure 12:
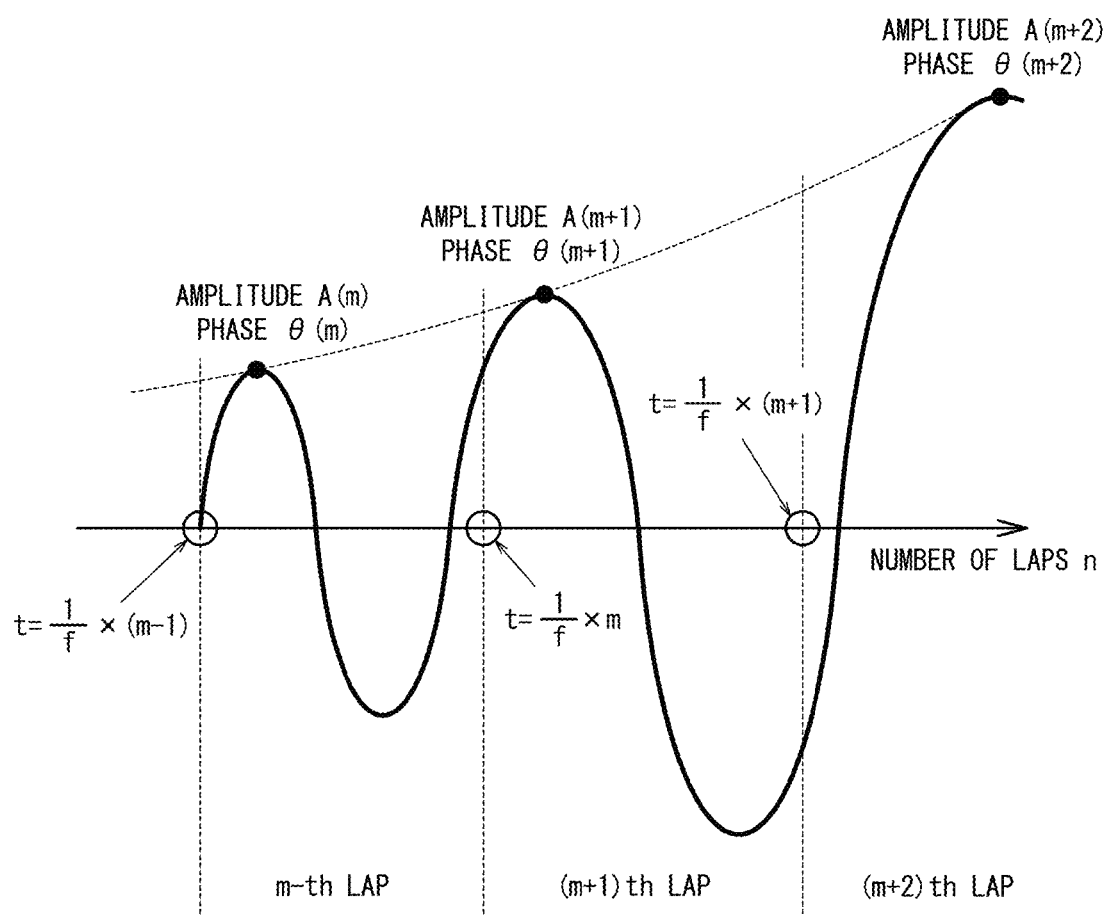
FIG. 12 shows the amplitude and the phase of a drive waveform for each lap.

This phenomenon may be quantitatively determined by fitting the phase $\theta(n)$ and the amplitude A(n) for each n number of laps, in the form of a function of $X = A \sin(2\pi ft + \theta)$, as illustrated in FIG. 12 for example.

That is, as illustrated in FIG. 12, when the drive frequency is f, fitting with the aforementioned equation may be performed for a drive waveform from the time $t = (1/f) \times (m-1)$ to $(1/f) \times m$, to thereby obtain the phase $\theta(m)$ and the amplitude A(m) in the m-th lap.

As an example of obtaining the phase shift and the amplitude in the X direction and the Y direction for each lap, described is a case of performing the fitting with the drive frequency: 3000 Hz, the modulation frequency: 15 Hz, the resonance frequency in the X direction: 3050 Hz, the resonance frequency in the Y-direction: 3100 Hz, the Q value in the X direction vibration: 500, and the Q value in the Y direction vibration 400.

The amplitude A(n) and the phase $\theta(n)$ in the X direction in the n-th lap may be obtained by, for example, polynomial fitting, which may be represented by Equations 7 and 8 below.

$$A_x(n) = a_6 \cdot n^6 + a_5 \cdot n^5 + a_4 \cdot n^4 + a_3 \cdot n^3 + a_2 \cdot n^2 + a_1 \cdot n + a_0 \quad \text{(Equation 7)}$$

$$\theta_x(n) = b_6 \cdot n^6 + b_5 \cdot n^5 + b_4 \cdot n^4 + b_3 \cdot n^3 + b_2 \cdot n^2 + b_1 \cdot n + b_0 \quad \text{(Equation 8)}$$

Accordingly, the spiral modulation pattern in the X direction can be represented as follows.

$$X(n) = A(n) \cdot \sin\{2\pi n + \theta_x(n)\} \quad \text{(Equation 9)}$$

$$(n = f \times t)$$

The pattern in the Y direction may similarly be obtained, to thereby derive the coefficients $a_6$ to $a_0$ and $b_6$ to $b_0$.

Figure 13A:
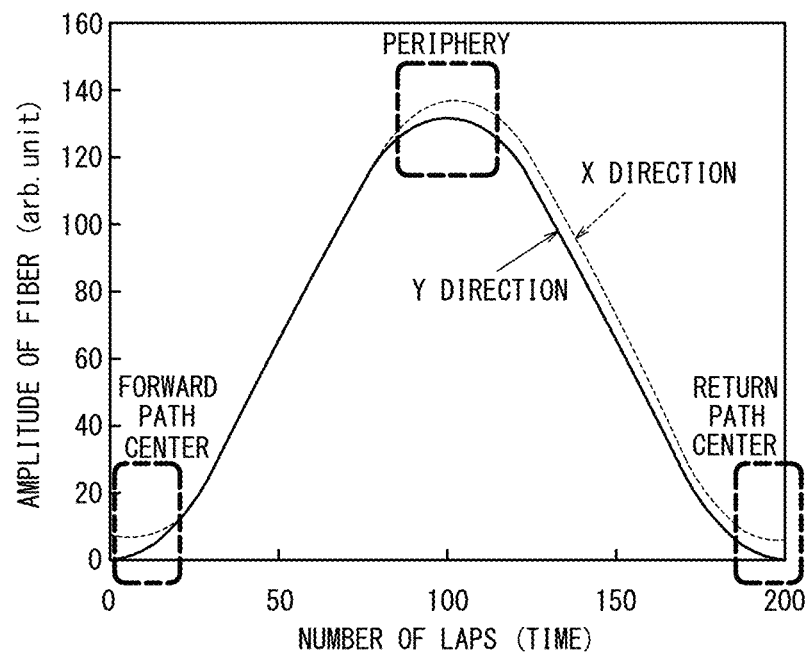
FIG. 13A is a graph showing variations in amplitude relative to the number of laps.
Figure 13B:
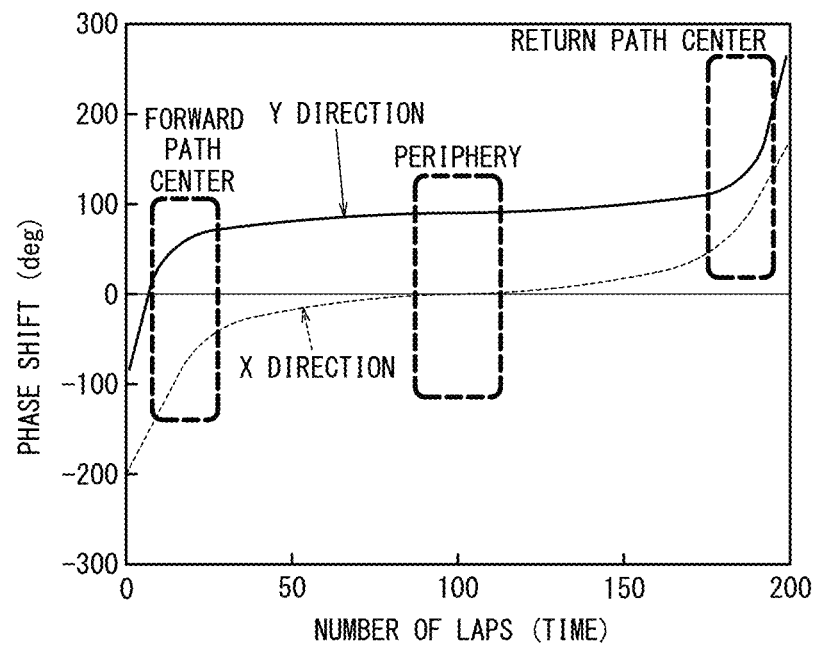
FIG. 13B is a graph showing variations in phase shift relative to the number of laps.

Here, FIGS. 13A and 13B each show, in a graph, the approximation functions of the amplitude and the phase thus obtained.

Figure 14A:
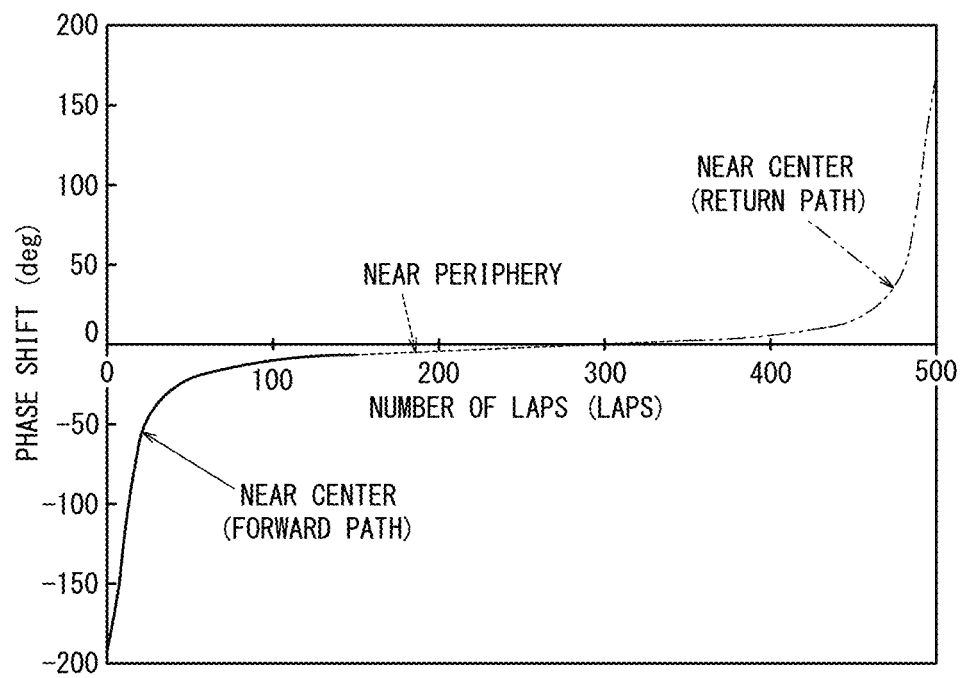
FIGS. 14A and 14B show variations in phase shift relative to the number of laps.
Figure 14B:
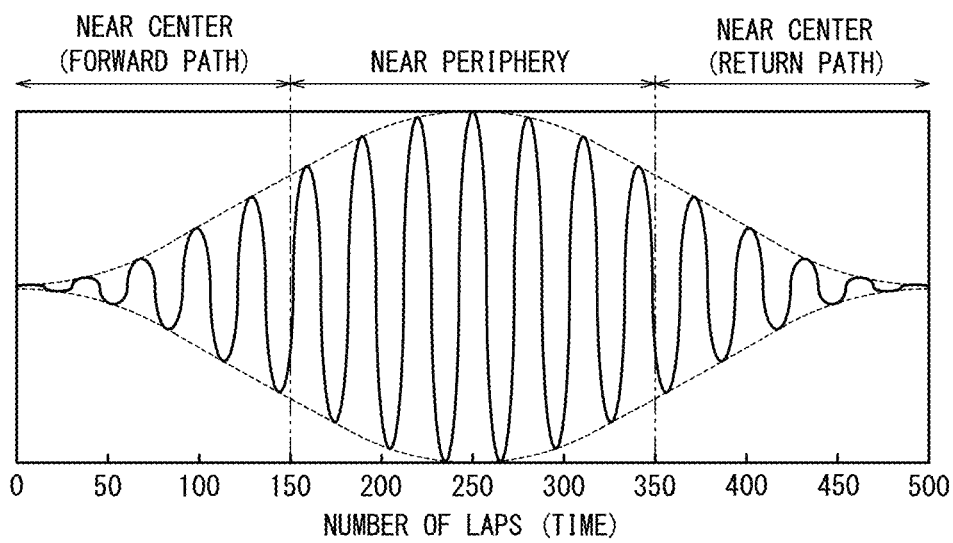

As another example, different fitting functions may separately be used for the center and the periphery of the pattern. That is, as illustrated in FIGS. 14A and 14B, the phase shift behavior is different between near the periphery and near the center, and thus, linear approximation may be applied near the periphery while polynomial approximation may be applied near the center.

Specifically, the phase shift $\theta(n)$ may be approximated by a polynomial (for example, fifth-order function) in the 0 to 150th laps (the forward path near the center), the phase shift $\theta(n)$ may be approximated by a first-order function in the 151st to 350th laps (near the periphery), and the phase shift θ(n) may be approximated by a polynomial (for example, fifth-order function) in the 351st to 500th laps (the return path near the center).

This way simplifies the function.

Then, the control/calculation part 31 may pass, to the image processor 37, information on the scanning pattern calculated based on information such as the amplitude and the phase of a vibration voltage applied by the drive control/resonance frequency detection part 38.

Described below is the operation and effect of the embodiment.

According to the optical scanning apparatus of this embodiment, first, the drive control/resonance frequency detection part 38 obtains in advance the resonance frequency of the oscillation part 11b of the optical fiber. The attenuation coefficient can also be obtained in advance by, for example, measuring impedance.

Then, the control/calculation part 31 calculates a scanning pattern based on the resonance frequency and the attenuation coefficient obtained in advance, and the scanning pattern thus calculated by the control/calculation part 31 may be used so as to use the position coordinate indicated by the scanning pattern, as position information during image processing.

This way allows the coordinate data to be obtained by merely determining the resonance frequency and the attenuation coefficient, without measuring the actual position coordinate at each time using PSD or the like. Thus, there is no need to store an enormous amount of data in a memory, which avoids restriction on the hardware. Further, the aforementioned resonance frequency and the attenuation coefficient can be measured by a simple method such as impedance measurement as described above.

Then, the calculated scanning pattern includes phase shift information, which eliminates image distortion (in particular, distortion in the direction of rotation).

Therefore, this embodiment allows for obtaining a high-quality image by a simple method.

Here, described below is an example of the scanning pattern calculated in practice using the optical scanning endoscope apparatus of FIG.

1. In the example, the drive frequency was defined to be smaller than the resonance frequency.

FIG. 15 shows a scanning pattern calculated when a spiral scan has been performed. In FIG. 15, the dot sequence A shows a phase shift in the Y-axis direction of the forward path from the center toward the periphery of the spiral, and the dot sequence B shows a phase shift in the Y-axis direction of the return path from the periphery toward the center of the spiral.

Further, FIG. 16A shows a drive pattern and FIG. 16B shows a relation between the number of laps and the phase, indicating, as an experimental result, the relation between the number of laps and the phase actually measured by the PSD.

First, as shown in FIG. 16A, the graph showing the relation between the number of laps and the phase shift obtained through calculation well matches with the experimental result.

This suggests that the disclosed control/calculation part 31 is capable of calculating the scanning pattern with accuracy.

Further, as shown in FIG. 16A, the phase shift becomes particularly significant in a position closer to the center than the periphery of the spiral.

In consideration thereof, as illustrated in FIG. 16B, when calculating the approximation function of phase change relative to time (the number of laps), second or higher-order polynomial approximation or exponential approximation may be performed at the center of the spiral (i.e., where the amplitude is equal to or lower than a certain value), while linear (first-order function) approximation may be performed in the periphery of the spiral (i.e., where the amplitude is larger than a certain value), to thereby perform approximation with further accuracy.

Further, in the disclosure, the approximation functions for the forward path and the return path of the spiral pattern may preferably be calculated independently of each other. The forward path and the return path may render different scanning loci, and thus, the separate calculation may further enhance the accuracy of approximation.

Further, the disclosed method and apparatus may be applied to a part of the scan. More specifically, the approximation function may preferably be calculated based on position data detected by the scanning position detector, when the amplitude of the oscillation part is equal to or lower than a certain value. The phase shift relative to an ideal scanning pattern is significant near the center of the scanning region, and thus the scanning pattern needs to be obtained with higher accuracy. Thus, the scanning position detector may be used in such range to obtain actual data to thereby obtain an accurate scanning pattern, while the scanning pattern may be calculated as described above in a range where the amplitude is large, to thereby suppress the memory capacity to minimum.

Alternatively, the scanning position detector may obtain actual data for the entire amplitude range and the data may be converted into a function using the aforementioned method, which can also similarly suppress the memory capacity.

Figure 17A:
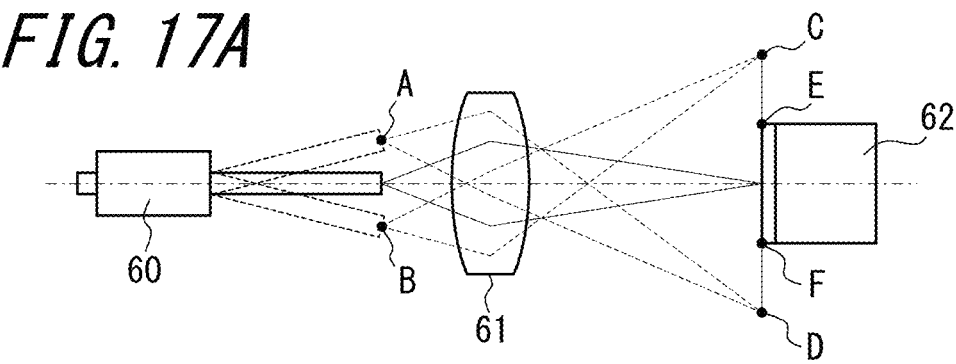
FIG. 17A shows an exemplary mechanism for measuring a scanning pattern.

Specifically, as illustrated in FIG. 17A, the oscillation part of the scanner 60 and the light receiving part of the PSD 62 may be designed to be optically conjugate to each other, and a laser spot light from the scanner 60 may be received by the PSD 62, to thereby obtain the scanning pattern of the fiber.

At this time, the magnifying power of the optical system 61 may be adjusted, so that the pattern range CD as the projection of the scanning range AB of the oscillation part of the fiber becomes larger than the light receiving range EF of the PSD 62, which allows for measuring the scanning pattern at the center of the spiral scanning region. When obtaining data across the entire range of amplitude, the magnifying power of the optical system 61 may be adjusted such that CD becomes smaller than EF.

Figure 17B:
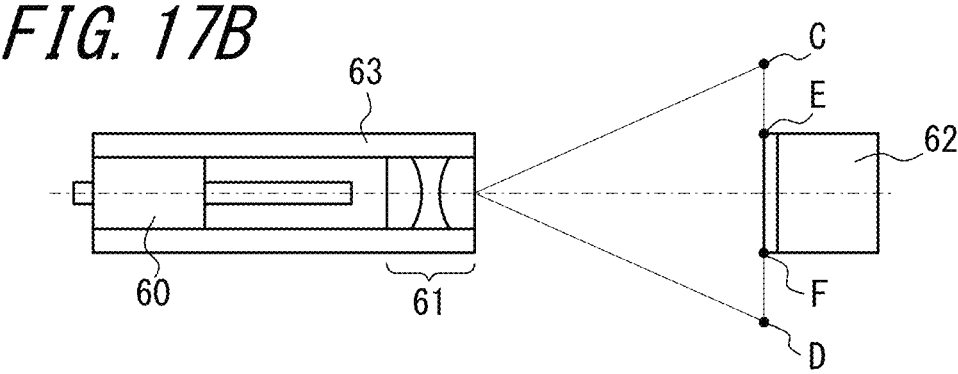
FIG. 17B shows another exemplary mechanism for measuring a scanning pattern.
Figure 17C:
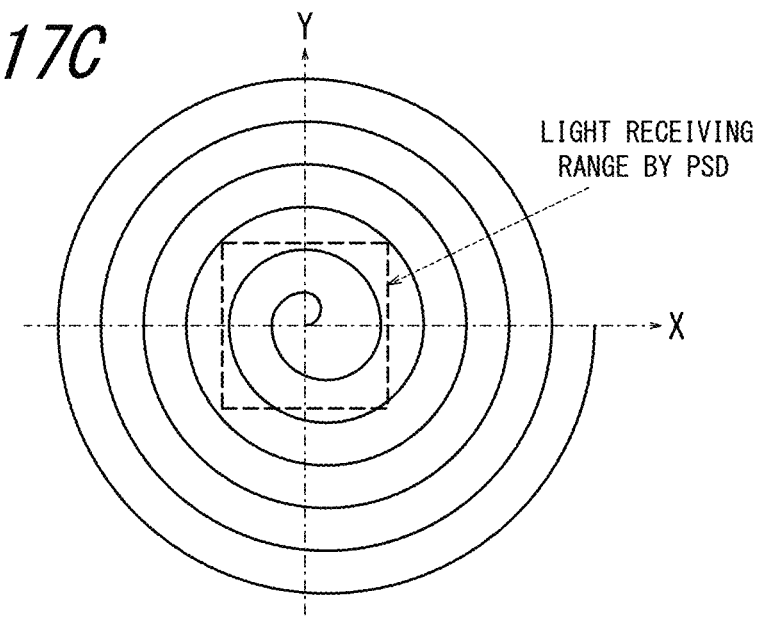
FIG. 17C shows a relation between a scanning pattern and the range of light received (light receiving range) by the PSD.

FIG. 17C illustrates the scanning pattern range and the light receiving range of the PSD, viewed from the optical axis direction.

Meanwhile, as illustrated in FIG. 17B, when evaluating a probe-like scanner where the optical system 61 and the oscillation part of the scanner 60 are integrally formed by means of a housing 63, the distance between the probe tip and the PSD may be properly adjusted, to thereby expand the pattern at the center of the scanning region so as to be measured with accuracy. The PSD detects the center of gravity of the laser spot light, and thus the fiber oscillation part of the fiber and the light receiving part of the PSD may not necessarily be conjugate to each other. When obtaining data across the entire range of amplitude, the distance between the probe tip and the PSD may be adjusted as appropriate such that CD becomes smaller than EF.

As described above, the scanning position can be detected with accuracy in a region where the amplitude is equal to or lower than a certain value.

For example, an image sensor may be used in place of the PSD, or the vibratory displacement of the oscillation part 11b of the fiber may be measured by a laser displacement meter.

Figure 18:
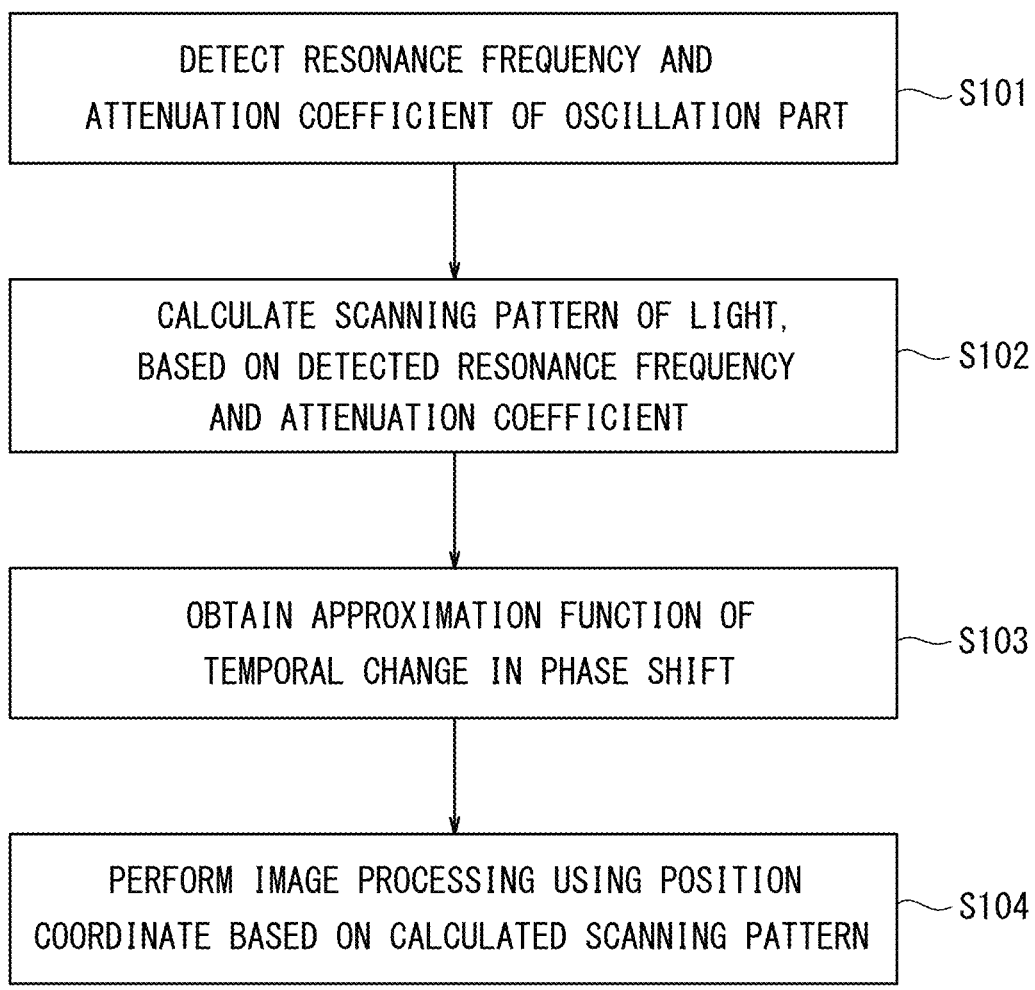
FIG. 18 is a flow chart of the disclosed method for calculating a scanning pattern of light according to an embodiment thereof.

FIG. 18 is a flow chart of the disclosed method of calculating a scanning pattern of light according to an embodiment thereof. As illustrated in FIG. 18, in this embodiment, the resonance frequency and the attenuation coefficient of the oscillation part of the optical fiber are first detected to be determined in advance by the aforementioned simple method for measuring impedance (Step S101). Then, based on the resonance frequency and the attenuation coefficient thus detected, the scanning pattern of light is calculated (Step S102). Here, the scanning pattern includes information on temporal change in phase shift, and thus, the approximation function of the pattern may also be obtained as appropriate (Step S103). Then, the position information on the scanning position of light based on the calculated scanning pattern (or the approximation function obtained in Step S103) may be used as the position coordinate for use in mapping during image formation, so as to process the image (Step S104). The method for calculating the scanning pattern of light according to this embodiment is capable of obtaining a high-quality image without imposing constraints on the hardware.

Here, in place of Steps S101 and S102, a scanning pattern actually measured by using PSD or the like may be used, which can reduce constraints to be imposed on the hardware as compared to storing all the scanning loci in a memory.

Alternatively, the scanning pattern of light under a plurality of drive conditions may be calculated in advance and a plurality of approximation coefficients may be obtained and memorized in hardware. The plurality of drive conditions may conceivably include the resonance frequency and the attenuation coefficient. It may be investigated and memorized in advance how the resonance frequency and the attenuation coefficient would change due to aged deterioration or changes in temperature and humidity in the use environment, and, for example, a temperature sensor may be disposed near the scanner so as to estimate the resonance frequency and the attenuation coefficient based on the temperature obtained by the temperature sensor, so that the optical scanning pattern and the approximation function may be read out from the memory based on the estimated drive conditions and applied to the image processing, which can alleviate distortion in the image due to temperature change with time.

Embodiments of the disclosed apparatus and method are described in the above, which in no way limit the present disclosure. For example, a spiral scan is exemplified in the embodiment above, but the present disclosure is also applicable to Lissajous scan and Raster scan. Further, in the case where the attenuation coefficient and the resonance frequency are already known, the detection step thereof is unnecessary, and the scanning pattern may be calculated by reading out the attenuation coefficient and the resonance frequency from a memory incorporated in the scope 20. Further, a method of driving the fiber using piezoelectric elements is illustrated in the specification, which in no way limits the fiber driving means, and other means such as electromagnetic drive means may similarly be used to obtain the same effect. The drive waveform may also be in other patterns than those described in the specification, which can still be expected to provide the same effect as long as the disclosed method is used.

REFERENCE SIGNS LIST 10 fiber scanning endoscope apparatus
11 illumination optical fiber
11a fixed end
11b oscillation part
11c emitting end
12 detection optical fiber
13 wiring cable
20 scope
21 actuator
22 operating portion
23 insertion portion
24 tip part
25 optical system
26 attachment ring
27 actuator tube
28a to 28d piezoelectric element
29 fiber holding member
30 control apparatus body
31 control/calculation part
32 emission timing controller
33R, 33G, 33B laser
34 coupler
35 photodetector
36 ADC
37 image processor
38 drive control/resonance frequency detection part
40 display
50 optical system
51 light detecting surface
52 optical scanning position detector
60 fiber scanner
61 optical system
62 PSD
63 housing
100 object

The invention claimed is:

1. A method for calculating a scanning pattern of light, comprising the steps of:
   detecting a resonance frequency and an attenuation coefficient of an oscillation part of an optical fiber which guides light from a light source and irradiates an object with the light; and
   calculating a scanning pattern of the light, based on the detected resonance frequency and attenuation coefficient.

2. The method for calculating a scanning pattern of light according to claim 1, wherein the scanning pattern includes information on temporal change in phase shift of the oscillation part.

3. The method for calculating a scanning pattern of light according to claim 2, further comprising the step of calculating an approximation function of the temporal change in phase shift.

4. A method for calculating a scanning pattern of light, comprising:
   detecting, using position data detected by a scanning position detector, a scanning pattern of light from an oscillation part of an optical fiber which guides the light from a light source and irradiates an object with the light; and calculating an approximation coefficient of temporal change in phase shift of the oscillation part included in the scanning pattern.

5. The method for calculating a scanning pattern of light according to claim 4, wherein the approximation function is an exponential function when the amplitude of the oscillation part is equal to or lower than a certain value, and is a first-order function when the amplitude is larger than the certain value.

6. The method for calculating a scanning pattern of light according to claim 4, wherein the approximation function is a second or higher-order polynomial function when the amplitude of the oscillation part is equal to or smaller than a certain value, and is a first-order function when the amplitude is larger than the certain value.

7. The method for calculating a scanning pattern of light according to claim 4, wherein the approximation function is calculated separately for the forward path and the return path of the scanning pattern.

8. The method for calculating a scanning pattern of light according to claim 4, wherein the approximation function depends on the drive frequency and/or the maximum amplitude of the oscillation part.

9. An optical scanning apparatus, comprising:
an optical fiber which guides light from a light source and irradiates an object with the light;
a drive control part which drives an oscillation part oscillatably supported of the optical fiber;
a resonance frequency detector which detects a resonance frequency of the oscillation part;
a calculation part which determines an irradiation position of the light using a scanning pattern calculated based on the resonance frequency detected by the detector and the attenuation coefficient obtained in advance.

10. The optical scanning apparatus according to claim 9, wherein the scanning pattern includes information on temporal change in phase shift of the oscillation part.

11. The optical scanning apparatus according to claim 10, wherein the calculation part calculates an approximation coefficient of the temporal change in phase shift.

12. An optical scanning apparatus, comprising:
an optical fiber which guides light from a light source and irradiates an object with the light;
a drive control part which drives an oscillation part oscillatably supported of the optical fiber; and
a calculation part which calculates, using position data detected by a scanning position detector, an approximation coefficient of temporal change in phase shift of the oscillation part included in the scanning pattern.

13. The optical scanning apparatus according to claim 12, wherein the approximation function is an exponential function when the amplitude of the oscillation part is equal to or smaller than a certain value, and is a first-order function when the amplitude is larger than the certain value.

14. The optical scanning apparatus according to claim 12, wherein the approximation function is a second or higher-order polynomial function when the amplitude of the oscillation part is equal to or smaller than a certain value, and is a first-order function when the amplitude is larger than the certain value.

15. The optical scanning apparatus according to claim 12, wherein the calculation part calculates the approximation function separately for the forward path and the return path of the scanning pattern.

16. The optical scanning apparatus according to claim 12, wherein the approximation function depends on the drive frequency and/or the maximum amplitude of the oscillation part.

17. The method for calculating a scanning pattern of light according to claim 3, wherein the approximation function is calculated separately in the case when the amplitude of the oscillation part is equal to or smaller than a certain value and in the case when the amplitude is larger than the certain value.

18. The method for calculating a scanning pattern of light according to claim 4, wherein the approximation function is calculated separately in the case when the amplitude of the oscillation part is equal to or smaller than a certain value and in the case when the amplitude is larger than the certain value.

19. The optical scanning apparatus according to claim 11, wherein the approximation function is calculated separately by the calculation part in the case when the amplitude of the oscillation part is equal to or smaller than a certain value and in the case when the amplitude is larger than the certain value.

20. The optical scanning apparatus according to claim 12, wherein the approximation function is calculated separately by the calculation part in the case when the amplitude of the oscillation part is equal to or smaller than a certain value and in the case when the amplitude is larger than the certain value.

* * * * *